US012257028B2

(12) United States Patent
Valsan et al.

(10) Patent No.: US 12,257,028 B2
(45) Date of Patent: Mar. 25, 2025

(54) ELECTRONIC DEVICES WITH BODY COMPOSITION ANALYSIS CIRCUITRY

(71) Applicant: Apple Inc., Cupertino, CA (US)

(72) Inventors: Gopal Valsan, Gilroy, CA (US); Thilaka S Sumanaweera, San Jose, CA (US); Liliana I Keats, Cupertino, CA (US); David J Feathers, Williamsville, NY (US); Pavan Kumar Anasosalu Vasu, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 226 days.

(21) Appl. No.: 17/865,194

(22) Filed: Jul. 14, 2022

(65) Prior Publication Data

US 2023/0065288 A1 Mar. 2, 2023

Related U.S. Application Data

(60) Provisional application No. 63/242,357, filed on Sep. 9, 2021, provisional application No. 63/238,714, filed on Aug. 30, 2021.

(51) Int. Cl.
*A61B 5/00* (2006.01)
*A61B 90/50* (2016.01)
(Continued)

(52) U.S. Cl.
CPC .......... *A61B 5/0077* (2013.01); *A61B 5/0075* (2013.01); *A61B 5/4872* (2013.01);
(Continued)

(58) Field of Classification Search
CPC ... A61B 5/0077; A61B 5/0075; A61B 5/4872; A61B 5/7267; A61B 5/7278;
(Continued)

(56) References Cited

U.S. PATENT DOCUMENTS 8,823,775 B2 9/2014 Xu et al.
9,665,906 B2 5/2017 Adeyoola et al.
(Continued)

FOREIGN PATENT DOCUMENTS

CN 111797249 A 10/2020
CN 112368628 A 2/2021
(Continued)

OTHER PUBLICATIONS

Abrevaya, V.F. et al. 2018. Multilinear Autoencoder for 3D Face Model Learning, IEEE, 2018 IEEE Winter Conference on Applications of Computer Vision (Year: 2018).*
(Continued)

*Primary Examiner* — Christopher L Cook
*Assistant Examiner* — Dean N Edun
(74) *Attorney, Agent, or Firm* — Treyz Law Group, P.C.; Kendall P. Woodruff

(57) ABSTRACT

An electronic device may include body composition analysis circuitry that estimates body composition based on captured images of a face, neck, and/or body (e.g., depth map images captured by a depth sensor, visible light and infrared images captured by image sensors, and/or other suitable images). The body composition analysis circuitry may analyze the image data and may extract portions of the image data that strongly correlate with body composition, such as portions of the cheeks, neck, waist, etc. The body composition analysis circuitry may encode the image data into a latent space. The latent space may be based on a deep learning model that accounts for facial expression and neck pose in face/neck images and that accounts for breathing and body pose in body images. The body composition analysis circuitry may output an estimated body composition based on the image data and based on user demographic information.

25 Claims, 11 Drawing Sheets

(51) Int. Cl.
*G06T 7/00* (2017.01)
*G06T 7/521* (2017.01)
*G16H 30/40* (2018.01)

(52) U.S. Cl.
CPC .......... *A61B 5/7267* (2013.01); *A61B 5/7278* (2013.01); *G06T 7/0012* (2013.01); *G06T 7/521* (2017.01); *G16H 30/40* (2018.01); *A61B 2090/502* (2016.02); *A61B 2576/02* (2013.01); *G06T 2207/10028* (2013.01); *G06T 2207/10048* (2013.01); *G06T 2207/20081* (2013.01); *G06T 2207/30201* (2013.01)

(58) Field of Classification Search
CPC .......... A61B 2090/502; A61B 2576/02; A61B 90/06; A61B 90/361; A61B 5/0059; A61B 5/0205; A61B 5/6898; A61B 5/4869; A61B 5/0033; A61B 5/1079; A61B 5/7445; G06T 7/0012; G06T 7/521; G06T 2207/10028; G06T 2207/10048; G06T 2207/20081; G06T 2207/30201; G06T 2207/10024; G06T 2207/20084; G16H 30/40; G16H 40/63; G16H 50/20; G16H 50/30; G16H 50/70
See application file for complete search history.

(56) References Cited

U.S. PATENT DOCUMENTS

| | | | |
|---|---|---|---|
| 10,702,216 | B2 | 7/2020 | Sareen et al. |
| 2016/0088284 | A1 | 3/2016 | Sareen et al. |
| 2016/0310071 | A1 | 10/2016 | Kim |
| 2017/0273639 | A1* | 9/2017 | Iscoe .................. G06N 20/00 |
| 2018/0144819 | A1 | 5/2018 | Lee et al. |
| 2018/0253840 | A1 | 9/2018 | Tran |
| 2019/0347817 | A1* | 11/2019 | Ferrantelli ............ G06F 18/217 |
| 2021/0006775 | A1* | 1/2021 | Kim .................... H04N 13/239 |
| 2021/0097759 | A1* | 4/2021 | Agrawal ............... G06T 15/005 |
| 2021/0287804 | A1* | 9/2021 | Barnes .................. G06T 7/0012 |
| 2022/0409128 | A1* | 12/2022 | Ayanbadejo, Sr. .. A61B 5/7475 |
| 2023/0005229 | A1* | 1/2023 | Kosecoff ................ G06V 40/16 |

FOREIGN PATENT DOCUMENTS

| | | |
|---|---|---|
| JP | 2008305261 A | 12/2008 |
| JP | 2009183418 A | 8/2009 |
| JP | 2014115821 A | 6/2014 |
| JP | 2015019867 A | 2/2015 |
| JP | 2015228256 A | 12/2015 |
| JP | 2020008929 A | 1/2020 |
| JP | 2020112900 A | 7/2020 |
| JP | 2020199072 A | 12/2020 |
| WO | 2021140731 A1 | 7/2021 |

OTHER PUBLICATIONS

Li, T. et al. Nov. 2017. Learning a model of facial shape and expression from 4D scans, ACM Transactions on Graphics, vol. 36, No. 6, Article 194. (Year: 2017).*
Tsoli, A. et al., Jul. 2014. Breathing Life into Shape: Capturing, Modeling and Animating 3D Human Breathing. ACM Transactions on Graphics, vol. 33, No. 4, 52, p. 1-11 (Year: 2014).*
Shao, H. et al. 2018. The Riemannian Geometry of Deep Generative Models. IEEE. 2018 IEEE/CVF Conference on Computer Vision and Pattern Recognition Workshops, pp. 428-436 (Year: 2018).*
Min Jiang et al., On visual BMI analysis from facial images, Image and Vision Computing, Aug. 1, 2019, pp. 1-14, Elsevier B.V . . . .
Antitza Dantcheva et al., Show me your face and I will tell you your height, weight and body mass index, 2018 24th International Conference on Pattern Recognition (ICPR), Aug. 20-24, 2018, pp. 3555-3560, IEEE, Beijing, China.
Pravin Mundada et al., Injectable facial fillers: imaging features, complications, and diagnostic pitfalls at MRI and PET CT, CrossMark, Oct. 4, 2017, pp. 1-16.
Jingjing Sun et al., Novel Body Shape Descriptors for Abdominal Adiposity Prediction Using Magnetic Resonance Images and Stereovision Body Images, www.obesityjournal.org, Aug. 26, 2017, pp. 1795-1801, vol. 25 No. 10, Obesity.

* cited by examiner

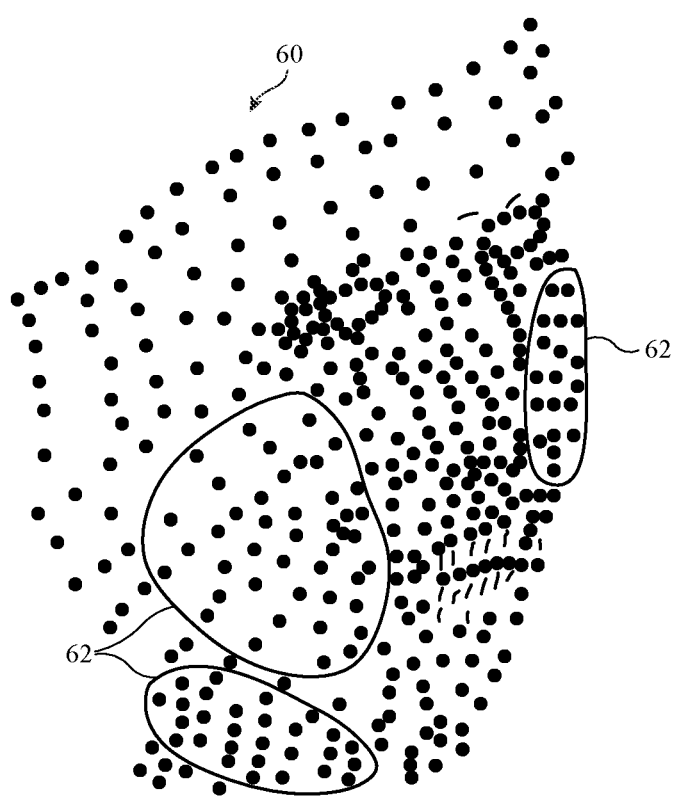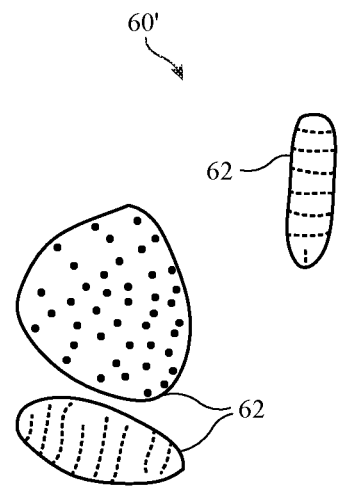
*FIG. 8*  *FIG. 9*

ELECTRONIC DEVICES WITH BODY COMPOSITION ANALYSIS CIRCUITRY

This application claims the benefit of provisional patent application No. 63/238,714, filed Aug. 30, 2021, and provisional patent application No. 63/242,357, filed Sep. 9, 2021, both of which are hereby incorporated by reference herein in their entireties.

FIELD

This relates generally to electronic devices, and, more particularly, to electronic devices with sensors.

BACKGROUND

Electronic devices such as cellular telephones, wristwatches, and other equipment are sometimes provided with sensors such as fingerprint sensors, facial recognition cameras, and heart rate sensors.

It can be challenging to use devices such as these. The user may wish to obtain different types of health-related information that traditional electronic devices are unable to provide. The user may need to rely on more than one piece of electronic equipment to obtain the desired health-related information, which can be inconvenient and cumbersome.

SUMMARY

An electronic device may include body composition analysis circuitry that estimates body composition based on captured images of a face, neck, and/or body (e.g., three-dimensional depth maps captured by a depth sensor, visible light and infrared images, and/or other suitable images). In some arrangements, a depth sensor in the electronic device may include an infrared light emitter that illuminates a face and neck with structured infrared light and an infrared light detector that detects infrared light reflected from the face and neck. The depth sensor may produce depth map image data capturing the three-dimensional structural data based on the reflected infrared light. Other types of depth sensing technology and/or visible light cameras may be used to capture face and neck image data, if desired. In some arrangements, the images may be full body images or may be images of a portion of a user's body such as the torso or bicep.

In some arrangements, the body composition analysis circuitry may use a user-study-trained model to map the images to body composition information. The model may be trained on images of a specific body part and/or may be trained on images of an entire body. The body composition information may describe how fat is distributed throughout the body and/or may describe relative amounts of fat in the visceral and subcutaneous compartments of the body. The body composition analysis circuitry may use images of the face to scale images of the body in order to determine dimensions of the body. The electronic device may be a head-mounted device or any other suitable electronic device that is worn or used by a first user while capturing images of a second user. The electronic device may also be self-operated while capturing images of the user. If desired, the electronic device may capture images of the user while attached to a stationary fixture.

The body composition analysis circuitry may analyze the image data and may extract portions of the image data that strongly correlate with body composition, such as portions of the cheeks, neck, face, chest, waist, hips, thighs, and other areas. The body composition analysis circuitry may encode the image data into a latent space. The latent space may be based on a deep learning model that is trained on user study data.

When using face images, the latent space may include a first latent space representing a user identity, a second latent space representing a facial expression, and a third latent space representing a neck pose. The body composition analysis circuitry may compensate for facial expression and neck pose by using the face and neck image data in the user identity latent space to output an estimated body composition.

When using body images, the latent space may include a first latent space representing a user identity, a second latent space representing a breathing state, and a third latent space representing a body pose. The body composition analysis circuitry may compensate for breathing state and body pose by using the body image data in the user identity latent space to output an estimated body composition.

The body composition analysis circuitry may use a user-study-trained model to map the images to body composition information. The model may be trained on images of a specific body part and/or may be trained on images of an entire body. The body composition information may describe how fat is distributed throughout the body and/or may describe relative amounts of visceral and subcutaneous fat in specific body parts. The body composition analysis circuitry may use images of the face to scale images of the body in order to determine dimensions of the body. The electronic device may be a head-mounted device or any other suitable electronic device that is worn by a first user while capturing images of a second user.

BRIEF DESCRIPTION OF THE DRAWINGS

FIG. 8 is a diagram of illustrative three-dimensional depth map image data associated with a face and neck in accordance with an embodiment.

FIG. 9 is a diagram showing how relevant portions of three-dimensional depth map image data of the type shown in FIG. 8 may be extracted for body composition analysis in accordance with an embodiment.

DETAILED DESCRIPTION

Figure 1:
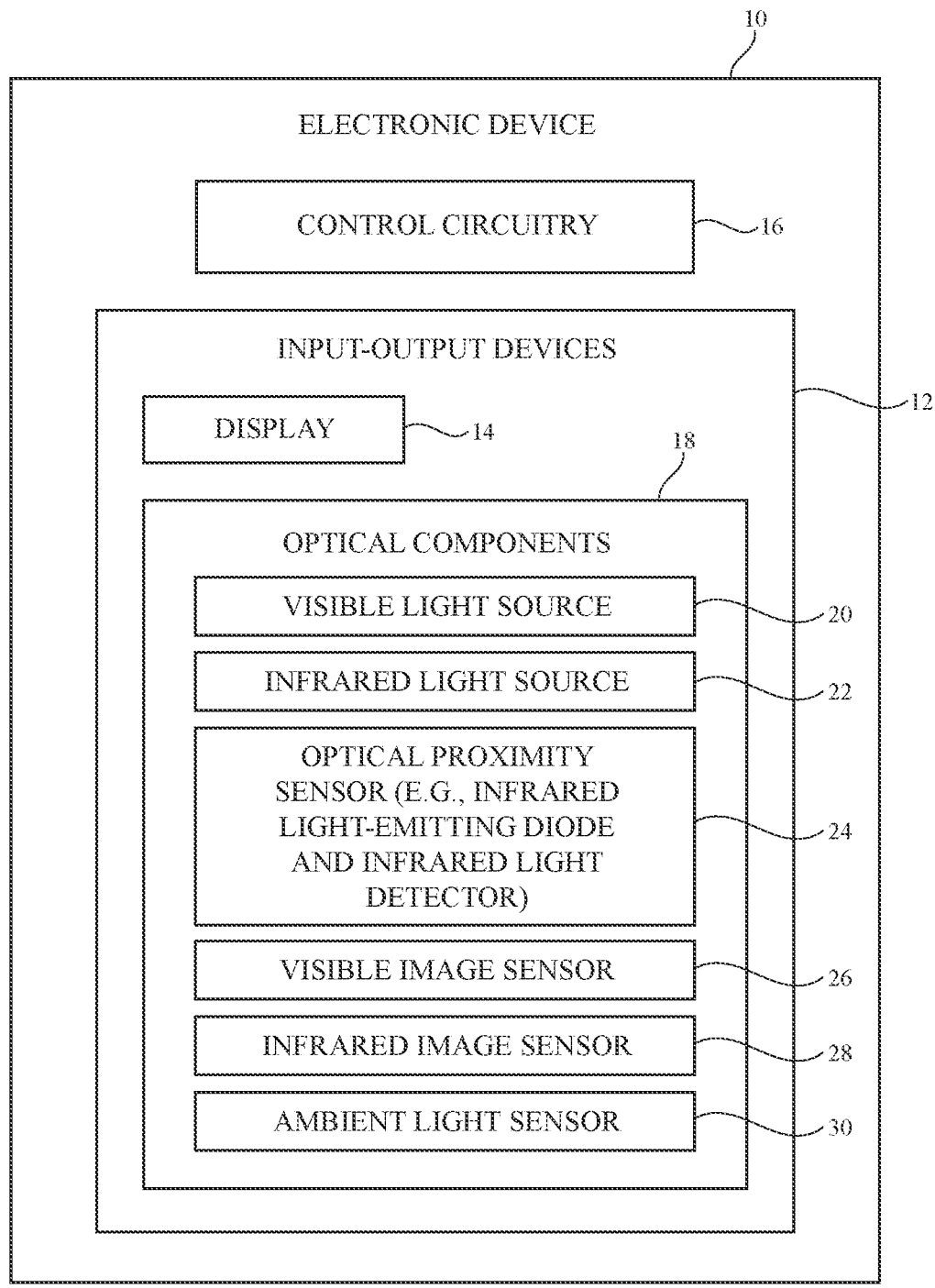
FIG. 1 is a schematic diagram of an illustrative electronic device in accordance with an embodiment.

A schematic diagram of an illustrative electronic device of the type that may be provided with an optical component is shown in FIG. 1. Electronic device 10 may be a computing device such as a laptop computer, a computer monitor containing an embedded computer, a tablet computer, a cellular telephone, a media player, or other handheld or portable electronic device, a speaker (e.g., a voice-controlled assistant or other suitable speaker), a smaller device such as a wristwatch device, a pendant device, a headphone or earpiece device, a device embedded in eyeglasses or other equipment worn on a user's head, or other wearable or miniature device, a television, a computer display that does not contain an embedded computer, a gaming device, a navigation device, an embedded system such as a system in which electronic equipment with a display is mounted in a kiosk or automobile, equipment that implements the functionality of two or more of these devices, or other electronic equipment.

As shown in FIG. 1, electronic device 10 may have control circuitry 16. Control circuitry 16 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 16 may be used to control the operation of device 10. The processing circuitry may be based on one or more microprocessors, microcontrollers, digital signal processors, baseband processors, power management units, audio chips, application specific integrated circuits, etc.

Device 10 may have input-output circuitry such as input-output devices 12. Input-output devices 12 may include user input devices that gather user input and output components that provide a user with output. Devices 12 may also include communications circuitry that receives data for device 10 and that supplies data from device 10 to external devices. Devices 12 may also include sensors that gather information from the environment.

Input-output devices 12 may include one or more displays such as display 14. Display 14 may be a touch screen display that includes a touch sensor for gathering touch input from a user or display 14 may be insensitive to touch. A touch sensor for display 14 may be based on an array of capacitive touch sensor electrodes, acoustic touch sensor structures, resistive touch components, force-based touch sensor structures, a light-based touch sensor, or other suitable touch sensor arrangements. Display 14 may be a liquid crystal display, a light-emitting diode display (e.g., an organic light-emitting diode display), an electrophoretic display, or other display.

Input-output devices 12 may include optical components 18. Optical components 18 may include light-emitting diodes and other light sources. As an example, optical components 18 may include one or more visible light sources such as light source 20 (e.g., a light-emitting diode). Light-emitting diode 20 may provide constant illumination (e.g., to implement a flashlight function for device 10) and/or may emit pulses of flash illumination for a visible light camera such as visible light image sensor 26. Optical components 18 may also include an infrared light source (e.g., a laser, lamp, infrared light-emitting diode, an array of vertical-cavity surface-emitting lasers (VCSELs), etc.) such as infrared light source 22. Infrared light source 22 may provide constant and/or pulsed illumination at an infrared wavelength such as 940 nm, a wavelength in the range of 800-1100 nm, etc. For example, infrared light source 22 may provide constant illumination for an infrared camera such as infrared image sensor 28. Infrared image sensor 28 may, as an example, be configured to capture iris scan information from the eyes of a user and/or may be used to capture images for a facial recognition process implemented on control circuitry 16.

If desired, infrared light source 22 may be used to provide flood illumination (e.g., diffused infrared light that uniformly covers a given area) and to provide structured light (e.g. a pattern of collimated dots). Flood illumination may be used to capture infrared images of external objects (e.g., to detect a user's face and/or to create a depth map), whereas structured light may be projected onto an external object to perform depth mapping operations (e.g., to obtain a three-dimensional map of the user's face). This is merely illustrative. Other types of depth sensors may be used, if desired (e.g., indirect time-of-flight sensors, stereo cameras, etc.).

To enable light source 22 to provide both flood illumination and structured light, light source 22 may include a switchable diffuser and a collimated light source such as a laser or an array of vertical cavity surface-emitting lasers. When flood illumination is desired, the diffuser may be turned on to diffuse the light from the light source. When structured illumination is desired, the diffuser may be turned off to allow the collimated light to pass through the diffuser uninhibited. Diffusers such as the diffuser in light source 22 may be formed from liquid crystal material, electrophoretic material, or other switchable light modulators. In some implementations, light source 22 projects light through a diffractive optical element (DOE) to create replicas of the pattern of dots. This is, however, merely illustrative. If desired, infrared light source 22 may include a first light source that provides flood illumination and a second light source that provides structured light.

Optical components 18 may also include optical proximity detector 24 and ambient light sensor 30.

Optical proximity detector 24 may include an infrared light source such as an infrared light-emitting diode and a corresponding light detector such as an infrared photodetector for detecting when an external object that is illuminated by infrared light from the light-emitting diode is in the vicinity of device 10.

Ambient light sensor 30 may be a monochrome ambient light sensor that measures the intensity of ambient light or may be a color ambient light sensor that measures ambient light color and intensity by making light measurements with multiple photodetectors each of which is provided with a corresponding color filter (e.g., a color filter that passes red light, blue light, yellow light, green light, or light of other colors) and each of which therefore responds to ambient light in a different wavelength band.

In addition to optical components 18, input-output devices 12 may include buttons, joysticks, scrolling wheels, touch pads, key pads, keyboards, microphones, speakers, tone generators, vibrators, cameras, light-emitting diodes and other status indicators, non-optical sensors (e.g., temperature sensors, microphones, capacitive touch sensors, force sensors, gas sensors, pressure sensors, sensors that monitor device orientation and motion such as inertial measurement units formed from accelerometers, compasses, and/or gyroscopes), data ports, etc. A user can control the operation of device 10 by supplying commands through input-output devices 12 and may receive status information and other output from device 10 using the output resources of input-output devices 12.

Figure 2:
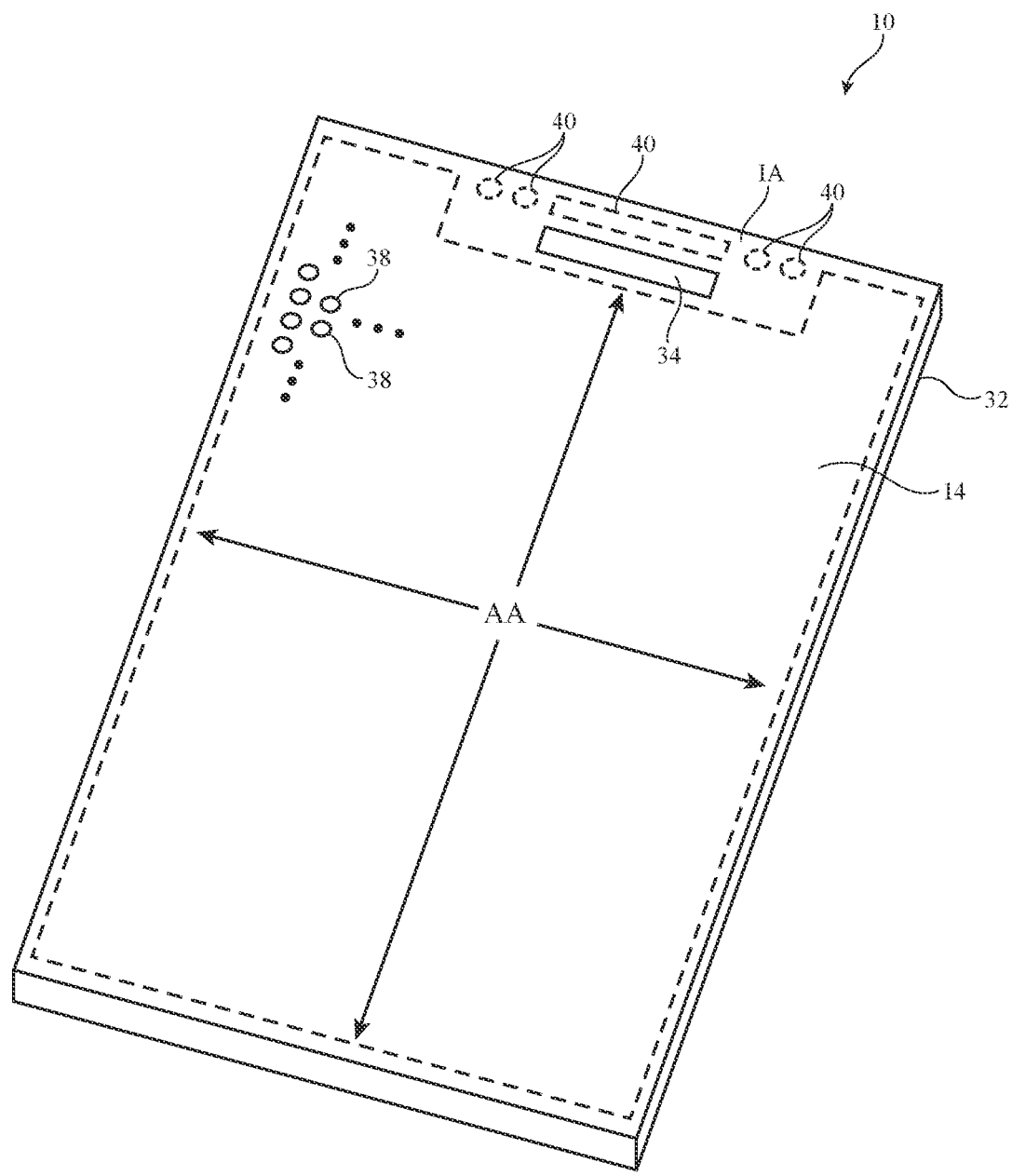
FIG. 2 is a perspective view of an illustrative electronic device with a display having optical component windows overlapping optical components in accordance with an embodiment.

Device 10 may have a housing. The housing may form a laptop computer enclosure, an enclosure for a wristwatch, a cellular telephone enclosure, a tablet computer enclosure, or other suitable device enclosure. A perspective view of a portion of an illustrative electronic device is shown in FIG. 2. In the example of FIG. 2, device 10 includes a display such as display 14 mounted in housing 32. Housing 32, which may sometimes be referred to as an enclosure or case, may be formed of plastic, glass, ceramics, fiber composites, metal (e.g., stainless steel, aluminum, etc.), other suitable materials, or a combination of any two or more of these materials. Housing 32 may be formed using a unibody configuration in which some or all of housing 32 is machined or molded as a single structure or may be formed using multiple structures (e.g., an internal frame structure, one or more structures that form exterior housing surfaces, etc.). Housing 32 may have any suitable shape. In the example of FIG. 2, housing 32 has a rectangular outline (footprint when viewed from above) and has four peripheral edges (e.g., opposing upper and lower edges and opposing left and right edges). Sidewalls may run along the periphery of housing 32. If desired, a strap may be coupled to a main portion of housing 32 (e.g., in configurations in which device 10 is a wristwatch or head-mounted device).

Display 14 may be protected using a display cover layer such as a layer of transparent glass, clear plastic, sapphire, or other clear layer (e.g., a transparent planar member that forms some or all of a front face of device 10 or that is mounted in other portions of device 10). Openings may be formed in the display cover layer. For example, an opening may be formed in the display cover layer to accommodate a button, a speaker port such as speaker port 34, or other components. Openings may be formed in housing 32 to form communications ports (e.g., an audio jack port, a digital data port, etc.), to form openings for buttons, etc. In some configurations, housing 32 may have a rear housing wall formed from a planar glass member or other transparent layer (e.g., a planar member formed on a rear face of device 10 opposing a front face of device 10 that includes a display cover layer).

Display 14 may have an array of pixels 38 in active area AA (e.g., liquid crystal display pixels, organic light-emitting diode pixels, electrophoretic display pixels, etc.). Pixels 38 of active area AA may display images for a user of device 10. Active area AA may be rectangular, may have notches along one or more of its edges, may be circular, may be oval, may be rectangular with rounded corners, and/or may have other suitable shapes.

Inactive portions of display 14 such as inactive border area IA may be formed along one or more edges of active area AA. Inactive border area IA may overlap circuits, signal lines, and other structures that do not emit light for forming images. To hide inactive circuitry and other components in border area IA from view by a user of device 10, the underside of the outermost layer of display 14 (e.g., the display cover layer or other display layer) may be coated with an opaque masking material such as a layer of black ink (e.g., polymer containing black dye and/or black pigment, opaque materials of other colors, etc.) and/or other layers (e.g., metal, dielectric, semiconductor, etc.). Opaque masking materials such as these may also be formed on an inner surface of a planar rear housing wall formed from glass, ceramic, polymer, crystalline transparent materials such as sapphire, or other transparent material.

In the example of FIG. 2, speaker port 34 is formed from an elongated opening (e.g., a strip-shaped opening) that extends along a dimension parallel to the upper peripheral edge of housing 32. A speaker may be mounted within device housing 32 in alignment with the opening for speaker port 34. During operation of device 10, speaker port 34 serves as an ear speaker port for a user of device 10 (e.g., a user may place opening 34 adjacent to the user's ear during telephone calls).

Optical components 18 (e.g., a visible digital image sensor, an infrared digital image sensor, a light-based proximity sensor, an ambient light sensor, visible and/or infrared light-emitting diodes that provide constant and/or pulsed illumination, etc.) may be mounted under one or more optical component windows such as optical component windows 40. In the example of FIG. 2, four of windows 40 have circular outlines (e.g., circular footprints when viewed from above) and one of windows 40 has an elongated strip-shaped opening (e.g., an elongated strip-shaped footprint when viewed from above). The elongated window 40 is mounted between the sidewall along the upper peripheral edge of device 10 and speaker port 34 and extends parallel to the upper peripheral edge of housing 32. If desired, windows such as optical windows 40 may have shapes other than circular and rectangular shapes. The examples of FIG. 2 are merely illustrative.

Optical component windows such as windows 40 may be formed in inactive area IA of display 14 (e.g., an inactive border area in a display cover layer such as an inactive display region extending along the upper peripheral edge of housing 32) or may be formed in other portions of device 10 such as portions of a rear housing wall formed from a transparent member coated with opaque masking material, portions of a metal housing wall, polymer wall structures, etc. In the example of FIG. 2, windows 40 are formed adjacent to the upper peripheral edge of housing 32 between speaker port opening 34 in the display cover layer for display 14 and the sidewall along the upper edge of housing 32. In some configurations, an opaque masking layer is formed on the underside of the display cover layer in inactive area IA and optical windows 40 are formed from openings within the opaque masking layer. To help optical windows 40 visually blend with the opaque masking layer, a dark ink layer, a metal layer, a thin-film interference filter formed from a stack of dielectric layers, and/or other structures may overlap windows 40.

Figure 3:
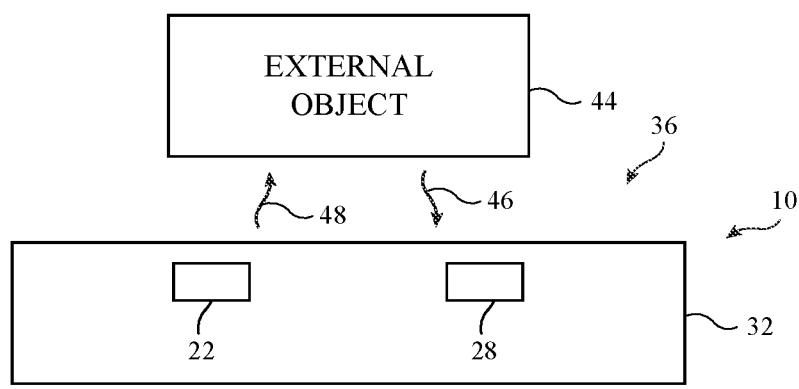
FIG. 3 is a cross-sectional side view of an illustrative electronic device that has optical components such as a light source and an image sensor in accordance with an embodiment.

An infrared emitter and infrared detector in device 10 may be used to form a three-dimensional depth sensor. FIG. 3 is a side view of an illustrative depth sensor 36 in device 10 that may be used to produce three-dimensional depth maps such as eye scan information, facial images (e.g., images of a user's face for use in performing facial recognition operations to authenticate the user of device 10, images of a user's face and neck for producing Animojis, etc.), body images (e.g., images of a user's body for use in performing motion tracking or body segmentation), and/or other three-dimensional depth mapping information. Depth sensor 36 may include infrared light emitter 22 and infrared light detector 28. Device 10 may use infrared light source 22 (e.g., an infrared light-emitting diode, an infrared laser, etc.) to produce infrared light 48. Light 48 may illuminate external objects in the vicinity of device 10 such as external object 44 (e.g., a user's face and/or eyes). Reflected infrared light 46 from external object 44 may be received and imaged using infrared digital image sensor 28 to produce infrared images (e.g., three-dimensional depth maps) of the face and/or eyes. Depth information may also be captured by applying appropriate software algorithms to visible and/or near-infrared videos and/or using any other suitable depth sensor in the device.

Infrared light source 22 may operate in different modes depending on the type of infrared information to be gathered by infrared camera 28. For example, in flood illumination mode, light source 22 may emit diffused light that uniformly covers a desired target area. In a structured light mode, light source 22 may emit a known pattern of light onto a desired target area.

Figure 4:
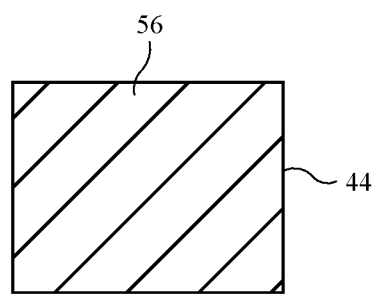
FIG. 4 is a cross-sectional side view of an illustrative light source that includes a diffuser in accordance with an embodiment.

FIG. 4 illustrates illumination from light source 22 when light source 22 is operated in a flood illumination mode. As shown in FIG. 4, light source 22 may emit diffused infrared light 56 that continuously covers a given area of external object 44. Infrared camera 28 may capture an infrared image of the diffusely illuminated external object 44. In some arrangements, flood illumination from light source 22 may be used to detect a user's face during face identification operations.

Figure 5:
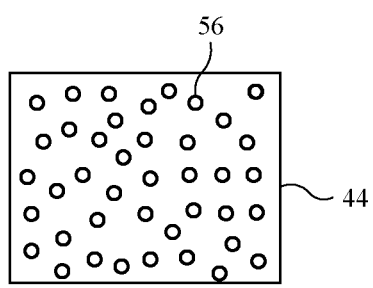
FIG. 5 is a front view of an illustrative object on which a dot pattern is projected using a light source of the type shown in FIG. 4 in accordance with an embodiment.

FIG. 5 illustrates illumination from light source 22 when light source 22 is operated in a structured light mode. In structured light mode, light source 22 may project a known pattern of infrared light 56 onto external object 44. In the example of FIG. 5, infrared light 56 forms a pattern of dots on external object 44. The dots may be in an ordered grid array (e.g., uniformly spaced from one another), or the dots may be projected in a random speckle pattern. This is, however, merely illustrative. If desired, light source 22 may emit structured light in other patterns (e.g., horizontal lines, vertical lines, a grid of horizontal and vertical lines, or other suitable predetermined pattern). Structured infrared light 56 of FIG. 5 may be based on laser interference or may be based on a projection display element that emits infrared light through a spatial light modulator to create the desired pattern.

In some arrangements, light source 22 may include one light source that provides flood illumination and another light source that provides structured light. In other arrangements, the same light source may be used to provide both flood illumination and structured light. This may be achieved using a switchable diffuser element that selectively diffuses light emitted from the light source.

Data that is gathered using optical components 18 may be used for one or more health-related applications such as body composition assessments. For example, control circuitry 16 may use optical components 18 to capture images of the user's face, neck, and/or body (e.g., visible images, infrared images, three-dimensional depth map images, etc.), which may then be analyzed to provide user-specific body composition information, such as body mass index, body fat percentage (e.g., fat percentage of the total body, fat percentage in individual body parts, and/or fat percentage in different fat storage compartments such as the subcutaneous and visceral compartments), bone mass, and/or other health-related information.

Control circuitry 16 may store one or more models for mapping user image data to body composition information. The model may be a statistical model, may be a machine learning model, may be a model based on a combination of statistical modeling and machine learning, or may be a combination of multiple machine learning models. Models that are trained using machine learning may be implemented using principal component analysis, an autoencoder, and/or any other suitable data compression technique.

An autoencoder is an artificial neural network that learns to encode data into a latent space by reducing the dimensions of the data. The autoencoder is trained to encode a distribution of inputs within a latent space to minimize loss between the outputs and the inputs. Principal component analysis reduces the dimensionality of input data by removing redundant information and capturing the most important features of the input data (e.g., features with the highest variance). Principal component analysis is generally restricted to linear mapping, whereas encoders do not have any linearity constraints.

Figure 6:
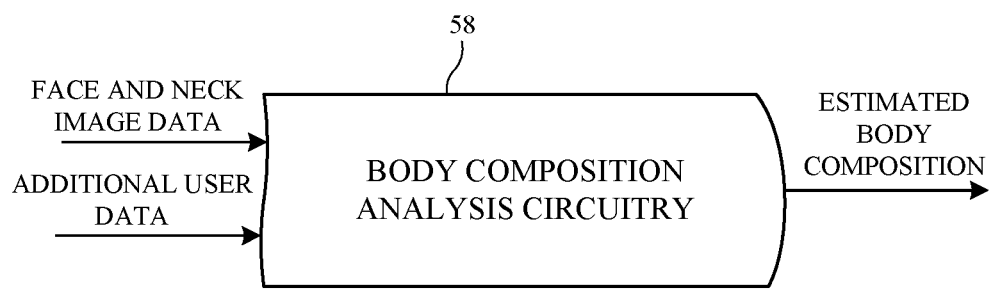
FIG. 6 is a schematic diagram of illustrative body composition analysis circuitry being used to analyze face and neck images in accordance with an embodiment.

FIG. 6 is a schematic diagram of body composition analysis circuitry 58 being used to determine body composition from face and/or neck images. Body composition analysis circuitry 58 may be part of control circuitry 16 and/or may be implemented as a standalone circuit. Body composition analysis circuitry 58 may receive information such as face and neck image data (e.g., three-dimensional depth map data of a user's face and/or neck from depth sensor 36, visible images of the user's face and/or neck from visible image sensor 26, etc.), and optional additional user data (e.g., user-specific demographic information such as gender, height, weight, age, ethnicity, and/or other user data stored in device 10 and/or otherwise provided to circuitry 58). Based on the received face and neck image data and optional user demographic data, body composition analysis circuitry 58 may output estimated body composition information such as body mass index, body fat percentage, fat percentage of the face and neck, bone mass, and/or other health-related information. If desired, user demographic information may be omitted and body composition analysis circuitry 58 may estimate the user's body composition based solely on the captured face and neck image data.

If desired, face and neck image data may be gathered as part of a dedicated body composition analysis (e.g., when depth sensor 36 is being used specifically for obtaining face and neck images for body composition analysis) and/or may be gathered when depth sensor 36 is already being used for some other purpose (e.g., when depth sensor 36 is already being used for facial recognition and user authentication purposes, when depth sensor 36 is already being used for creating an Animoji or other virtual reality applications that involve capturing a user's facial expressions, etc.). The face and neck image data may include one or more images that are captured of the face and neck at different times of the day and/or over multiple days.

User demographic information may be received from the user as part of a dedicated body composition analysis questionnaire and/or may be received from the user as part of some other health-related application.

Body composition analysis circuitry 58 may store a model that is trained using data from user studies. For example, data may be collected from a group of participants (e.g., ten participants, fifty participants, one hundred participants, one thousand participants, and/or any other suitable number of participants) over a given period of time (e.g., one month, two months, three months, six months, eight months, ten months, a year, more than a year, less than a year, etc.). At each point of data collection during the study, the study participant's face and neck shape and size may be measured and the user's body composition may be measured. Face and neck shape and size may be measured using a three-dimensional depth sensor of the type shown in FIG. 3, using anthropometric measurements (e.g., body landmarks and measurements) and/or using any other suitable measuring device (e.g., a three-dimensional body scanner). Body composition may be measured using any suitable body composition tracking technology such as magnetic resonance imaging, dual energy X-ray absorptiometry, air displacement plethysmography, underwater weighing, etc. Alternatively, a model can be trained to predict fat percentage in the face and the neck. Data collected during the user study may serve as training data for training the model that is stored in body composition analysis circuitry 58 in device 10.

Body composition analysis circuitry 58 may use principal component analysis, an autoencoder, and/or any other suitable data compression technique to reduce the dimensionality of the input data in a latent space. For example, the latent space may include an identity latent space that describes the identity of the subject, an expression latent space that describes the facial expressions of the subject, and a pose latent space that describes the neck pose of the subject. By including a facial expression latent space and a neck pose latent space, body composition analysis circuitry 58 can compensate for effects of facial expression and neck pose by using the identity latent space only to output an estimated body composition of the subject. Additionally, transfer learning methods can be used to selectively enhance pre-trained machine learning models using other data.

Figure 7:
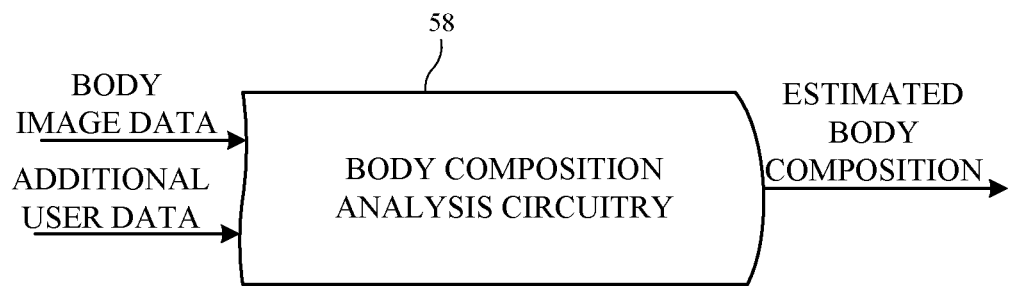
FIG. 7 is a schematic diagram of illustrative body composition analysis circuitry being used to analyze body images in accordance with an embodiment.

FIG. 7 is a schematic diagram of body composition analysis circuitry 58 being used to determine body composition. Body composition analysis circuitry 58 may be part of control circuitry 16 and/or may be implemented as a standalone circuit. Body composition analysis circuitry 58 may receive information such as body image data (e.g., three-dimensional depth map data of a user's body from depth sensor 36, visible images of the user's body from visible image sensor 26, etc.), and optional additional user data (e.g., user-specific demographic information such as gender, height, weight, age, ethnicity, and/or other user data stored in device 10 and/or otherwise provided to circuitry 58). Based on the received body image data and optional user demographic data, body composition analysis circuitry 58 may output estimated body composition information such as body mass index, body fat percentage, bone mass, and/or other health-related information. If desired, user demographic information may be omitted and body composition analysis circuitry 58 may estimate the user's body composition based solely on the captured body image data.

Body composition analysis circuitry 58 may analyze body composition using any suitable model. In a two-compartment model, the body is assumed to be made up of two compartments, a first compartment corresponding to fat and a second compartment corresponding to everything other than fat (e.g., muscle, bone, etc.). In a three-compartment model, the body is assumed to be made up of visceral fat, subcutaneous fat, and non-fat. If desired, body composition analysis circuitry 58 may use a three-compartment model and may estimate an amount of visceral fat, subcutaneous fat, and non-fat in a user based on images of the user. Body composition analysis circuitry 58 may estimate body composition of specific regions of the body (e.g., how much visceral fat and subcutaneous fat is located in a user's torso) or may estimate body composition across the entire body (e.g., how a total amount of visceral fat and subcutaneous fat is distributed across the user's body).

If desired, body image data may be gathered as part of a dedicated body composition analysis (e.g., when depth sensor 36 is being used specifically for obtaining body images for body composition analysis) and/or may be gathered when depth sensor 36 is already being used for some other purpose (e.g., when depth sensor 36 is already being used for some other body scanning purpose). The body image data may include one or more images that are captured of the body from different views (e.g., front view, side profile view, back view, etc.) at different times of the day and/or over multiple days. The image data may include a sequence of images, such as those from a video taken while the subject is breathing and/or moving.

User demographic information may be received from the user as part of a dedicated body composition analysis questionnaire and/or may be received from the user as part of some other health-related application.

Body composition analysis circuitry 58 may store a model that is trained using data from user studies. For example, data may be collected from a group of participants (e.g., ten participants, fifty participants, one hundred participants, one thousand participants, and/or any other suitable number of participants) over a given period of time (e.g., one month, two months, three months, six months, eight months, ten months, a year, more than a year, less than a year, etc.). At each point of data collection during the study, the study participant's body shape and size may be measured and the user's body composition may be measured. Body shape and size may be measured using a three-dimensional depth sensor of the type shown in FIG. 3, using anthropometric measurements (e.g., body landmarks and measurements) and/or using any other suitable measuring device (e.g., a three-dimensional body scanner). Body composition may be measured using any suitable body composition tracking technology such as magnetic resonance imaging, dual energy X-ray absorptiometry, air displacement plethysmography, underwater weighing, etc. Alternatively, a model can be trained to predict fat percentage in the body. Data collected during the user study may serve as training data for training the model that is stored in body composition analysis circuitry 58 in device 10.

Body composition analysis circuitry 58 may use principal component analysis, an autoencoder, and/or any other suitable data compression technique to reduce the dimensionality of the input data in a latent space. For example, the latent space may include an identity latent space that describes the identity of the subject, a breathing state latent space that describes the breathing state of the subject, and a pose latent space that describes the body pose of the subject. By including a breathing state latent space and a body pose latent space, body composition analysis circuitry 58 can compensate for effects of breathing and body pose by using the identity latent space only to output an estimated body composition of the subject. Additionally, transfer learning methods can be used to selectively enhance pre-trained machine learning models using other data.

The model that body composition analysis circuitry 58 uses to map image data to body composition may take into account various factors to help distinguish fat from fluids. Body composition analysis circuitry 58 may use known regions of fat and water storage to differentiate between fat and fluid accumulation. For example, bags under the eyes may be an indicator of fluid retention rather than fat storage. Areas around the joints, feet, and arms tend to be fluid retention areas rather than fat storage areas.

FIG. 8 is a diagram showing illustrative data that may be used to determine body composition when using face and/or neck image data. As shown in FIG. 8, captured image data 60 (e.g., captured face and neck image data) may include a three-dimensional depth map of a user's face and neck. The face and neck image data 60 may include an array of data points representing the depth to different locations across the user's face and neck. Image data 60 may be captured by depth sensor 36 of FIG. 3, if desired.

If desired, all of image data 60 may be used during body composition analysis operations, or only a portion of image data 60 may be used during body composition analysis operations. Because body fat tends to be stored in certain fat pockets such as regions in the cheeks and neck, those regions may be more indicative of body composition than other regions. For example, the shape of a user's forehead may exhibit little variation as a user's body fat changes, whereas portions of the cheeks and neck may exhibit detectable changes that directly correlate to changes in body composition. If desired, body composition analysis circuitry 58 may select certain portions of data 60 such as data in regions 62 for body composition analysis and may delete the remaining data from device 10. After selecting data in regions 62 and deleting the remaining data, body composition analysis circuitry 58 may proceed with body composition analysis using data 60' of FIG. 9.

Figure 10:
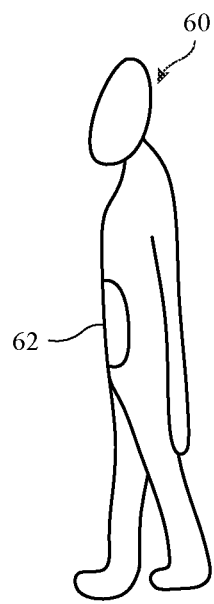
FIG. 10 is a diagram of illustrative image data corresponding to a side body view in accordance with an embodiment.
Figure 11:
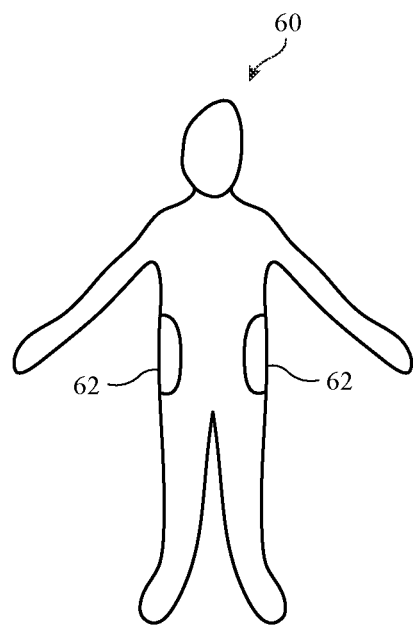
FIG. 11 is a diagram of illustrative image data corresponding to a front body view in accordance with an embodiment.

FIGS. 10 and 11 are diagrams showing illustrative data that may be used to determine body composition when using body images. As shown in FIG. 10, captured image data 60 (e.g., captured body image data 60) may include one or more three-dimensional depth maps of a user's body captured from a side view. FIG. 11 shows how captured body image data 60 may include one or more three-dimensional depth maps of a user's body captured from a front view. The body image data 60 may include an array of data points representing the depth to different locations across the user's body. Image data 60 may be captured by depth sensor 36 of FIG. 3, if desired. This is merely illustrative, however. If desired, image data 60 may be depth image data captured by a different type of depth sensor (e.g., one that does not use structured light, for example), may be visible light image data captured using a visible light camera, may be infrared image data captured by an infrared sensor, or may be other suitable image data.

In some arrangements, data 60 may be gathered using a sensor in device 10 that is placed sufficiently far away from the user to capture a full body image. For example, device 10 may be a television having a sensor that captures image data 60 while a user is standing sufficiently far away to capture a full body image, or device 10 may be a portable electronic device such as a cellular telephone, a laptop, a tablet computer, or other electronic device that can be propped up in one location to capture full body images of a user while the user stands at a distance. If desired, device 10 may be a head-mounted device or any other suitable electronic device that a first user (e.g., a physical trainer) wears while viewing a second user (e.g., a client of the trainer) at a distance. The head-mounted device may have a sensor that captures image data 60 of the second user while the second user stands at a distance from the first user wearing device 10. The electronic device may be self-operated while capturing images of the user. If desired, the electronic device may be attached to a stationary fixture while capturing images of the user.

In some arrangements, data 60 may be gathered by a handheld electronic device that is held in the user's hand (e.g., using a front-facing image sensor in device 10). Image distortion may be corrected for using pincushion distortion rectification, keystone correction, and/or any other suitable distortion compensation techniques. If desired, images of the user's face that do not exhibit distortion may be used to remove distortion in full body images. For example, the dimensions of a user's face may be determined from a face image that does not have distortion, which in turn may be used to scale a full body image so that control circuitry 16 can determine the dimensions of the user's body based on the full body image. Orientation information from motion sensors in device 10 (e.g., accelerometers, gyroscopes, compasses, etc.) may also be used to remove distortion from full body images to get a more accurate picture of the size of a user's body. Arrangements in which body composition analysis circuitry 58 stitches together multiple photos of different parts of the body may also be used.

In some arrangements, image data 60 may include images of only a portion of the user's body. For example, image data 60 may be torso image data that includes images of the user's torso only, bicep image data that includes images of the user's bicep, leg image data that includes images of the user's legs only, and/or other suitable image data. Images of a certain portion of the user's body may be used to determine body composition in that particular portion of the user's body (e.g., to track visceral and/or subcutaneous fat in the torso, bicep, etc.).

Figure 12:
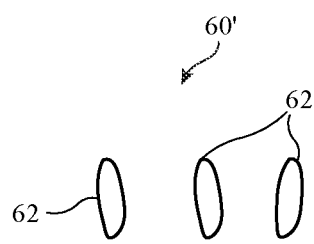
FIG. 12 is a diagram showing how relevant portions of image data of the type shown in FIGS. 10 and 11 may be extracted for body composition analysis in accordance with an embodiment.

If desired, all of image data 60 may be used during body composition analysis operations, or only a portion of image data 60 may be used during body composition analysis operations. Because body fat tends to be stored in certain fat pockets such as regions in the face, neck, waist, hips, and thighs, those regions may be more indicative of body composition than other regions. For example, the shape of a user's forehead may exhibit little variation as a user's body fat changes, whereas portions of the cheeks, neck, and waist may exhibit detectable changes that directly correlate to changes in body composition. If desired, body composition analysis circuitry 58 may determine which portions of data 60 correspond to regions of the body that strongly correlate with body composition such as data in regions 62 and may delete the remaining data from device 10. After selecting data in regions 62 and deleting the remaining data, body composition analysis circuitry 58 may proceed with body composition analysis using data 60' of FIG. 12.

Figure 13:
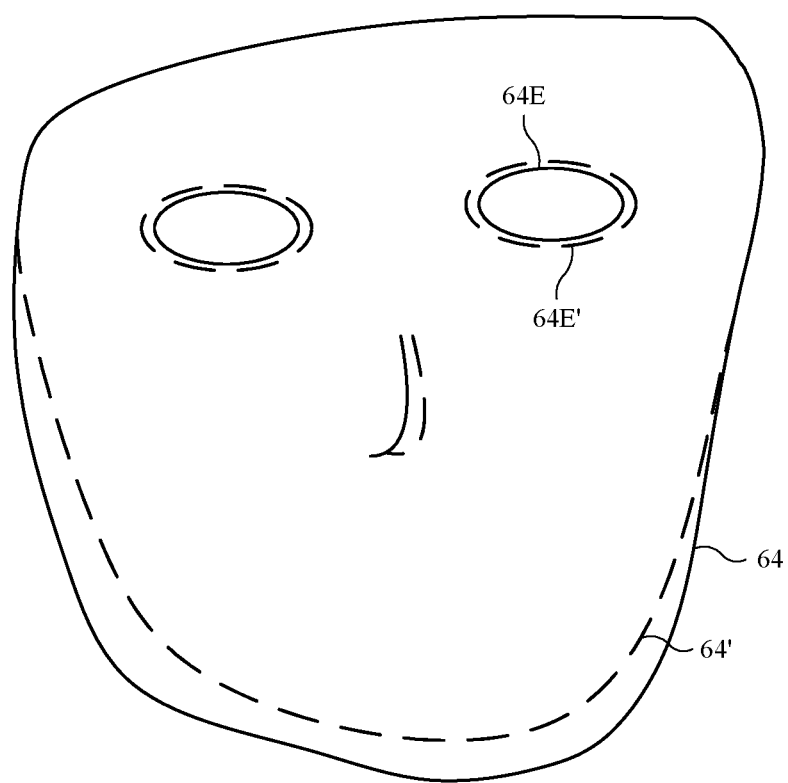
FIG. 13 is a diagram illustrating how face image data captured at different times may be aligned for body composition analysis in accordance with an embodiment.

If desired, body composition analysis circuitry 58 may track changes in body composition over time by comparing face, neck, and/or body images that are captured at different times. FIG. 13 is a diagram illustrating how body composition analysis circuitry 58 may compare face images captured at different times. As shown in FIG. 13, image 64 may represent an image captured by depth sensor 36 at a first time, while image 64' may represent an image captured by depth sensor 36 at a second time. In order to track body composition changes between the first and second times, body composition analysis circuitry 58 may align portions of image 64 and image 64' that are least expected to change over time. For example, a user's eyes, nose, ears, and/or other facial features may exhibit little change over time and can therefore serve as good anchors for aligning images captured at different times. As shown in FIG. 13, for example, body composition analysis circuitry 58 may align eyes 64E of image 64 with eyes 64E' of image 64', thereby allowing body composition analysis circuitry 58 to more accurately track changes in shape and size to other regions of the face such as the user's cheek and neck. If desired, body composition analysis circuitry 58 may store a model that maps changes in face and neck shape and size to changes in body composition (e.g., body composition analysis circuitry 58 may map the difference between image 64 and image 64' to a corresponding change in body fat, if desired).

Figure 14:
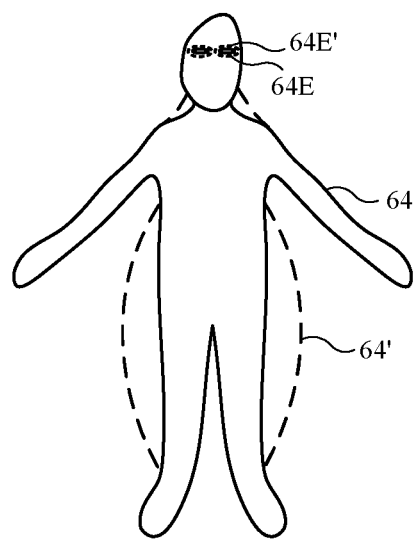
FIG. 14 is a diagram illustrating how body image data captured at different times may be aligned for body composition analysis in accordance with an embodiment.

FIG. 14 is a diagram illustrating how body composition analysis circuitry 58 may compare body images captured at different times. As shown in FIG. 14, image 64 may represent an image captured by depth sensor 36 at a first time, while image 64' may represent an image captured by depth sensor 36 at a second time. In order to track body composition changes between the first and second times, body composition analysis circuitry 58 may align portions of image 64 and image 64' that are least expected to change over time. For example, a user's eyes, nose, ears, other facial features, and limb and/or skeletal lengths may exhibit little change over time and can therefore serve as good anchors for aligning images captured at different times. As shown in FIG. 14, for example, body composition analysis circuitry 58 may align eyes 64E of image 64 with eyes 64E' of image 64', thereby allowing body composition analysis circuitry 58 to more accurately track changes in shape and size to other regions of the body such as the user's face, neck, and waist. If desired, body composition analysis circuitry 58 may store a model that maps changes in body shape and size to changes in body composition (e.g., body composition analysis circuitry 58 may map the difference between image 64 and image 64' to a corresponding change in body fat, if desired).

Figure 15:
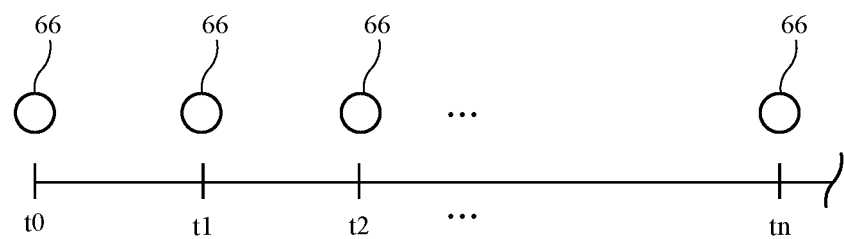
FIG. 15 is a diagram of illustrative user study data that may be gathered over a period of time in accordance with an embodiment.

FIG. 15 is a diagram illustrating how data may be collected during one or more user studies for training a model that is stored in body composition analysis circuitry 58 in device 10. As shown in FIG. 15, data 66 may be collected from a given population of users at time t0, time t1, time t2, etc., up to time tn. Data 66 may include measurements of the participants' face, neck, and/or body shape and size and measurements of the participants' body fat. Data 66 may be collected once per day, once per week, once per month, or at any other suitable cadence throughout the user study. The study may extend over a period of one month, two months, three months, six months, eight months, ten months, a year, more than a year, less than a year, etc.

At each point of data collection during the study (e.g., at times t0, t1, t2, . . . tn), each participant's face, neck, and/or body shape and size may be measured and the participant's body composition may be measured. Training data may include full body measurements and/or may include segmental body measurements (e.g., bicep measurements, torso measurements, leg measurements, etc.). Training the model that is stored in device 10 based on segmental body data may allow for a user to track changes to a specific body part. For example, the user may use device 10 to take a picture of the user's bicep, and body composition analysis circuitry 58 may map the bicep image to a muscle mass value based on bicep training data included in data 66.

Face, neck, and/or body shape and size may be measured using a three-dimensional depth sensor of the type shown in FIG. 3, using anthropometric measurements (e.g., using landmarks and measurements) and/or using any other suitable measuring device (e.g., a three-dimensional body scanner). Body composition may be measured using any suitable body composition tracking technology such as magnetic resonance imaging, dual energy X-ray absorptiometry, air displacement plethysmography, underwater weighing, etc. Fat data may be measured using a localized method such as magnetic resonance imaging or dual energy X-ray absorptiometry (e.g., to obtain body fat of body parts such as limbs, torso, lower abdomen, upper abdomen, chest, neck, head, and face), for example. Data 66 collected during the user study may serve as training data for training the model that is stored in body composition analysis circuitry 58 in device 10. If desired, images of a given participant's face, neck, and/or body captured at different times throughout the study may be aligned and compared using a technique of the type described in connection with FIGS. 13 and 14.

Figure 16:
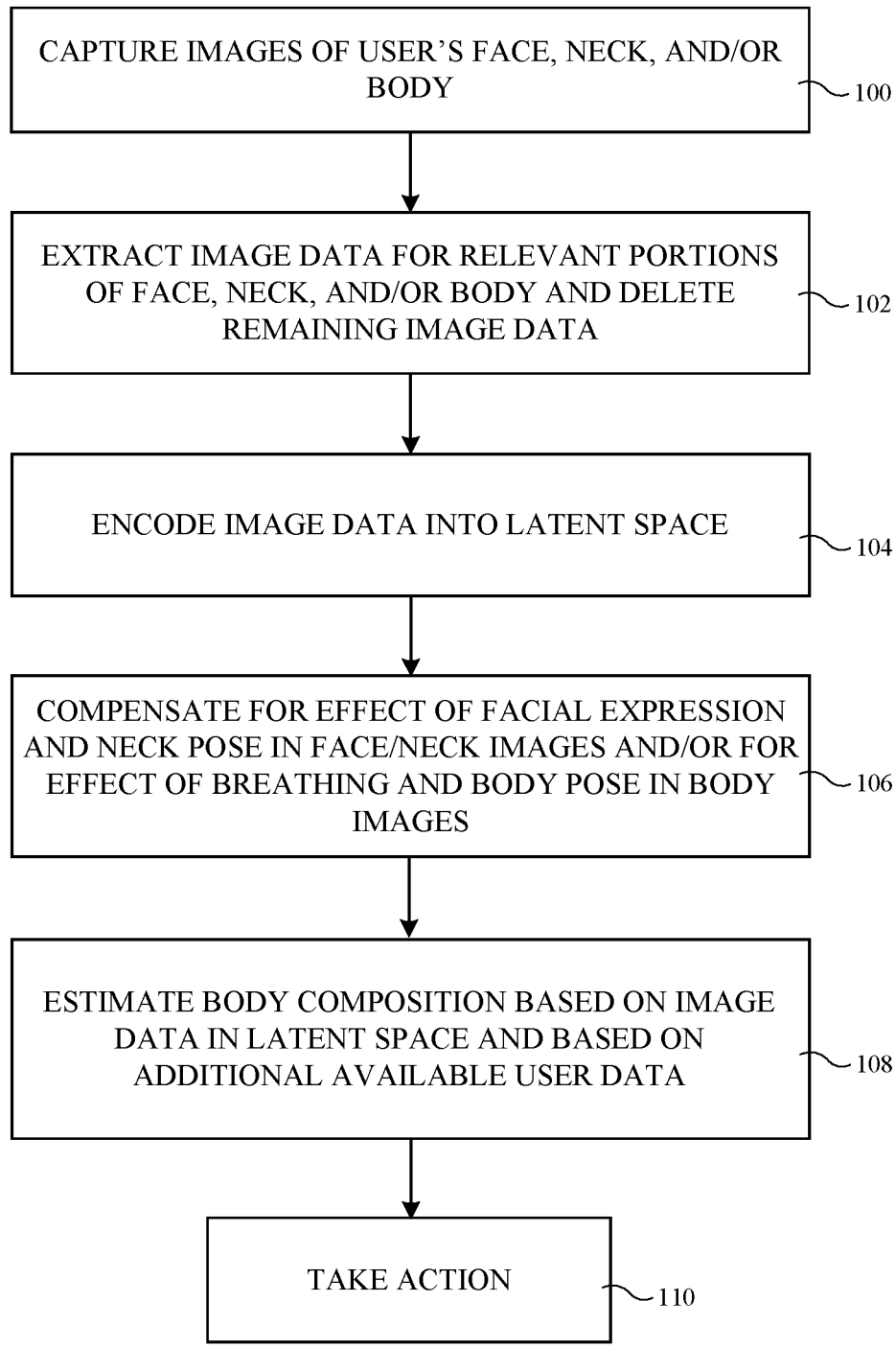
FIG. 16 is a flow chart of illustrative steps involved in estimating body composition based on captured image data in accordance with an embodiment.

FIG. 16 is a flow chart of illustrative steps involved in estimating a user's body composition based on captured images during the operation of device 10.

During the operations of block 100, body composition analysis circuitry 58 may use one or more optical components 18 in device 10 to capture one or more images of a user's face, neck, and/or body. For example, depth sensor 36 may capture a three-dimensional depth map image of the user's face, neck, and/or body, visible image sensor 26 may capture a visible image of the user's face, neck, and/or body, and/or other optical components 18 in device 10 may be used to gather image data of the user's face, neck, and/or body.

For body images, image data may be captured by scanning the body from head to feet, by capturing the entire body in one image frame, and/or by capturing multiple image frames of different parts of the body such as the face, neck, waist, legs, etc. The body image data may include a side body view and a front body view, as illustrated in FIGS. 10 and 11. The image data may also be captured in a sequence of images, such as those from a video taken while the subject is breathing and/or moving.

The face, neck, and/or body image data may be gathered as part of a dedicated body composition analysis (e.g., when depth sensor 36 is being used specifically for obtaining face, neck, and/or body images for body composition analysis) and/or may be gathered when depth sensor 36 is already being used for some other purpose (e.g., when depth sensor 36 is already being used for facial recognition and user authentication purposes, when depth sensor 36 is already being used for creating an Animoji or other virtual reality applications that involve capturing a user's facial expressions, etc.). The face, neck, and/or body image data may include one or more images that are captured of the face, neck, and/or body from different perspectives, at different times of the day, and/or over multiple days.

During the operations of block 102, body composition analysis circuitry 58 may analyze the images captured during block 100 and may identify which regions of the captured images are relevant for body composition analysis. This may include identifying which regions of the image data correspond to regions that strongly correlate with body composition (e.g., regions 62 of FIGS. 8, 9, 10, 11, and 12). Image data corresponding to face regions (e.g., cheek regions), neck regions, and/or waist regions, for example, may be preserved for body composition analysis. Regions of the image data that do not strongly correlate with body composition may be deleted or otherwise unused, if desired.

During the operations of block 104, body composition analysis circuitry 58 may encode the relevant image data identified during block 102 into a latent space. This may include reducing the dimensionality of the image data using an autoencoder, principal component analysis, and/or other data compression technique. For example, if the relevant image data for body composition includes thousands of data points, body composition analysis circuitry 58 may compress the relevant image data to hundreds of data points (as an illustrative example).

For face and neck images, the latent space may include an identity latent space that describes the identity of the subject, an expression latent space that describes the facial expressions of the subject, and a pose latent space that describes the neck pose of the subject. The latent space may be based on statistical modeling, deep learning techniques (e.g., autoencoders, primary component analysis, etc.), and/or may be based on a combination of statistical modeling and deep learning.

For body images, the latent space may include an identity latent space that describes the identity of the subject, a breathing state latent space that describes the breathing state of the subject, and a body pose latent space that describes the body pose of the subject. The latent space may be based on statistical modeling, deep learning techniques (e.g., autoencoders, primary component analysis, etc.), and/or may be based on a combination of statistical modeling and deep learning.

During the operations of block 106, body composition analysis circuitry 58 may compensate for the effect of facial expression and neck pose in face/neck images by extracting the identity latent space only (e.g., removing the expression latent space and neck pose latent space). For body images, body composition analysis circuitry 58 may compensate for the effect of breathing and body pose by extracting the identity latent space only (e.g., removing the breathing state latent space and body pose latent space).

During the operations of block 108, body composition analysis circuitry 58 may estimate body composition based on the image data in the identity latent space. For example, using a model trained on one or more user studies (e.g., as described in connection with FIGS. 6 and 7), body composition analysis circuitry 58 may map the compressed image data (e.g., a compressed data set representing the size and/or shape of the user's cheeks and neck, a compressed data set representing the size and/or shape of the user's waist, etc.) to body composition information such as body mass index, body fat percentage (e.g., fat percentage of the total body, fat percentage in individual body parts, and/or fat percentage in different fat storage compartments such as the subcutaneous and visceral compartments), bone mass, and/or other health-related information. The body composition information provided by body composition analysis circuitry 58 may be an estimated current body composition value (e.g., a body fat percentage value, a body mass index value, or bone mass value) and/or may be an estimated change in some body composition parameter (e.g., an amount of increase or decrease in a given body composition parameter such as body mass index, body fat percentage, bone mass, etc.). If desired, body composition analysis circuitry 58 may also take into account any available user demographic information (e.g., gender, height, weight, age, ethnicity, and/or other user data stored in device 10 and/or otherwise provided to circuitry 58) to determine the body composition of the user.

Body composition analysis circuitry 58 may analyze body composition using any suitable model. In a two-compartment model, the body is assumed to be made up of two compartments, a first compartment corresponding to fat and a second compartment corresponding to everything other than fat (e.g., muscle, bone etc.). In a three-compartment model, the body is assumed to be made up of visceral fat, subcutaneous fat, and non-fat. If desired, body composition analysis circuitry 58 may use a three-compartment model and may estimate an amount of visceral fat, subcutaneous fat, and non-fat in a user based on images of the user.

During the operations of block 108, body composition analysis circuitry 58 may estimate body composition of specific regions of the body (e.g., how much visceral fat and subcutaneous fat is located in a user's torso, bicep, or other body part) or may estimate body composition across the entire body (e.g., how a visceral fat and subcutaneous fat is distributed across the user's body).

The operations of block 108 may include removing distortion from images of the body (e.g., perspective distortion that is created when the user points a front-facing camera downwards to capture the whole body in one frame). Body composition analysis circuitry 58 may also use images of the user's face (e.g., previously gathered face images such as face images that are gathered during user identification operations and/or face images that are captured specifically for body composition analysis) to scale full body images (e.g., body dimensions may be determined based on a fully body image and a face image, using the face image for scale). Orientation information from motion sensors in device 10 (e.g., accelerometers, gyroscopes, compasses, etc.) may also be used to remove distortion from full body images to get a more accurate picture of the size of a user's body. Arrangements in which body composition analysis circuitry 58 stitches together multiple photos of different parts of the body may also be used.

During the operations of block 110, control circuitry 16 can take action in response to the analysis results. For example, device 10 can provide the assessment results to a user of device 10 and/or may issue an alert for the user of device 10 (e.g., if the assessment results suggest a risk of disease, for example). In general, notifications can be issued, databases can be updated, recommendations may be provided, and/or other actions may be taken based on the results of the sensor processing operations of block 108. For example, display 14 may display the estimated body fat percentage value, body mass index value, bone mass value, and/or other information determined by body composition analysis circuitry 58. Notifications may include text notifications, audible alerts, email messages, annotated images, other on-screen notification content on display 14, and/or other notification content.

As described above, one aspect of the present technology is the gathering and use of information such as information from input-output devices. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

The foregoing is merely illustrative and various modifications can be made to the described embodiments. The foregoing embodiments may be implemented individually or in any combination.

What is claimed is:

1. An electronic device, comprising:
a sensor that captures an image of a face and neck; and
body composition analysis circuitry that:
encodes a portion of the image into a latent space, wherein the latent space includes a first latent space representing a user identity, a second latent space representing a facial expression, and a third latent space representing a neck pose; and
determines a fat percentage value based on the portion of the image, wherein the body composition analysis circuitry compensates for the facial expression and the neck pose by removing the second and third latent spaces and using the first latent space to determine the fat percentage value based on the portion of the image.

2. The electronic device defined in claim 1 wherein the latent space is based on a statistical model.

3. The electronic device defined in claim 1 wherein the latent space is based on a deep learning model.

4. The electronic device defined in claim 1 wherein the sensor comprises a depth sensor and the image comprises a three-dimensional depth map image, the depth sensor comprising:
an infrared light source that illuminates the face and neck with structured light; and
an infrared light detector that detects the structured light that reflects from the face and neck.

5. The electronic device defined in claim 1 wherein the portion of the image includes a cheek portion and a neck portion.

6. The electronic device defined in claim 5 wherein the body composition analysis circuitry deletes a remaining portion of the image that is not encoded into the latent space.

7. The electronic device defined in claim 1 wherein the body composition analysis circuitry maps the portion of the image to the fat percentage value based at least partly on user demographic data.

8. The electronic device defined in claim 1 wherein the sensor comprises a visible light camera and the image comprises a visible light image.

9. An electronic device, comprising:
an infrared light source that illuminates a face with structured light;
an infrared light detector that detects the structured light that reflects from the face and that outputs corresponding depth information;
body composition analysis circuitry that encodes the depth information into a latent space and maps the depth information to body composition information, wherein the latent space includes a first latent space representing a user identity, a second latent space representing a facial expression, and a third latent space representing a neck pose, and wherein the body composition analysis circuitry compensates for the facial expression and the neck pose by removing the second and third latent spaces and using the first latent space to map the depth information to the body composition information; and a display that displays the body composition information.

10. The electronic device defined in claim 9 wherein the latent space is based on a deep learning model that is trained with user study data.

11. The electronic device defined in claim 9 wherein the body composition analysis circuitry deletes an unused portion of the depth information.

12. An electronic device, comprising:
a three-dimensional depth sensor that captures face and neck image data; and
control circuitry that:
receives the face and neck image data;
encodes the face and neck image data into a latent space, wherein the latent space includes a first latent space representing a user identity, a second latent space representing a facial expression, and a third latent space representing a neck pose;
receives user demographic information; and
determines an estimated body composition based on the face and neck image data and the user demographic information, wherein the control circuitry compensates for the facial expression and the neck pose by removing the second and third latent spaces and using the first latent space to determine the estimated body composition.

13. The electronic device defined in claim 12 wherein the control circuitry uses a portion of the face and neck image data to determine the estimated body composition and deletes a remaining portion of the face and neck image data.

14. The electronic device defined in claim 12 further comprising a display that displays the estimated body composition.

15. The electronic device defined in claim 12 wherein the latent space is based on a deep learning model that is trained with user study data.

16. An electronic device, comprising:
a sensor that captures an image of a body; and
body composition analysis circuitry that:
encodes the image into a latent space that includes a first latent space representing a user identity, a second latent space representing a breathing state, and a third latent space representing a body pose; and
uses a user-study-trained model to map the image of the body to body composition information, wherein the user-study-trained model accounts for variations due to breathing and pose by removing the second and third latent spaces and using the first latent space to map the image of the body to the body composition information.

17. The electronic device defined in claim 16 wherein the sensor captures an image of a face and wherein the body composition analysis circuitry uses the image of the face to scale the image of the body to determine dimensions of the body.

18. The electronic device defined in claim 16 wherein the body composition information indicates how body fat is distributed throughout the body.

19. The electronic device defined in claim 16 wherein the body composition information includes a visceral fat percentage and a subcutaneous fat percentage.

20. The electronic device defined in claim 16 wherein the user-study-trained model is selected from the group consisting of: a statistical model and a deep learning model.

21. The electronic device defined in claim 16 further comprising head-mounted support structures.

22. The electronic device defined in claim 21 wherein the sensor captures the image of the body of a first user while the head-mounted support structures are worn on a head of a second user.

23. The electronic device defined in claim 16 wherein the sensor comprises an infrared depth sensor and the image of the body is an infrared depth map image.

24. The electronic device defined in claim 16 wherein the sensor comprises a visible light camera and the image of the body is a visible light image.

25. The electronic device defined in claim 16 wherein the image of the body is an image of only a portion of the body and wherein the body composition information describes body composition of the portion of the body.

* * * * *